(12) United States Patent
Carr et al.

(10) Patent No.: US 9,046,486 B2
(45) Date of Patent: Jun. 2, 2015

(54) SECURITY ASPECTS OF MULTIEXPONENTIAL DECAYS

(75) Inventors: Paul A. Carr, Dallas, TX (US); Jeffrey L. Conroy, Allen, TX (US); Olusola O. Soyemi, Plano, TX (US)

(73) Assignee: Authentix, Inc., Addison, TX (US)

( * ) Notice: Subject to any disclaimer, the term of this patent is extended or adjusted under 35 U.S.C. 154(b) by 381 days.

(21) Appl. No.: 13/534,798

(22) Filed: Jun. 27, 2012

(65) Prior Publication Data

US 2014/0001351 A1    Jan. 2, 2014

(51) Int. Cl.
   *G01N 21/64* (2006.01)

(52) U.S. Cl.
   CPC .... *G01N 21/6428* (2013.01); *G01N 2021/6439* (2013.01); *G01N 21/6458* (2013.01); *G01N 21/6408* (2013.01)

(58) Field of Classification Search
   CPC ................. G01N 21/6428; G01N 21/6458
   USPC ............................................ 250/458.1, 459.1
   See application file for complete search history.

(56) References Cited

U.S. PATENT DOCUMENTS

| | | | |
|---|---|---|---|
| 2005/0178841 A1* | 8/2005 | Jones et al. | 235/468 |
| 2007/0095891 A1* | 5/2007 | Giering et al. | 235/379 |
| 2007/0295116 A1* | 12/2007 | Le Mercier et al. | 73/866 |
| 2008/0048106 A1* | 2/2008 | Blanchard et al. | 250/252.1 |
| 2009/0008454 A1* | 1/2009 | Jones et al. | 235/462.01 |
| 2012/0256409 A1* | 10/2012 | Giering et al. | 283/85 |

* cited by examiner

*Primary Examiner* — David Porta
*Assistant Examiner* — Mindy Vu

(57) ABSTRACT

At least two luminescent materials are intermingled within a security feature. The materials are selected from among a larger set of luminescent materials each having a different individual exponential decay characteristic (decay constant and initial amplitude response to the degree of excitation) for photo-luminescent emission from the respective material following excitation. The ratio of the decay constants for any two materials is greater than or equal to about 1.5. The selected materials are mixed in one of a plurality of predetermined ratios. The combined emissions from the intermingled materials appear, to an unsophisticated measuring device, to have a single exponential decay constant. Based on measurements for the decay of the combined emissions following excitation, estimates of the individual decay constants and associated initial emission amplitudes allow decoding of the particular combination of materials and/or their ratios to validate the security feature, authenticating the article.

20 Claims, 5 Drawing Sheets

SECURITY ASPECTS OF MULTIEXPONENTIAL DECAYS

TECHNICAL FIELD

The present disclosure relates generally to use of luminescent materials for authentication and, more specifically, to exploiting combinations of quasi-resonant luminescent materials with identical or distinct emission wavelengths.

BACKGROUND

Authentication of items such as documents, especially banknotes (currency) and the like, against forgery or counterfeiting may involve detection of the exponential decay from photoluminescence. In particular, time resolved emissions from quasi-resonant materials, which emit light having a similar wavelength to the excitation source, tend to be dominated by an exponential function of time (t) having the general form $$y = Ae^{-t/\tau} \quad (1)$$

where A (the amplitude) describes the intensity of the signal at time t and $\tau$ (the lifetime of the decay) provides an identifier for the specific quasi-resonant luminescent material. Security features including such materials, though proven, are growing more ubiquitous and therefore less reliable for authentication of very high security features such as those on banknotes and security documents.

There is, therefore, a need in the art for improved security features for authentication.

SUMMARY

At least two luminescent materials are intermingled within a security feature. The materials are selected from among a larger set of luminescent materials each having a different individual exponential decay characteristic (decay constant and initial amplitude response to the degree of excitation) for photo-luminescent emission from the respective material following excitation. The ratio of the decay constants for any two materials is greater than or equal to about 1.5. The selected materials are mixed in one of a plurality of predetermined ratios. As a result of mixture, the combined emissions from the intermingled materials appear, to an unsophisticated measuring device, to have a single exponential decay constant. Based on measurements for the decay of the combined emissions following excitation, estimates of the individual decay constants and associated initial emission amplitudes allow decoding of the particular combination of materials and/or their ratios to validate the security feature, authenticating the article including the security feature.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 5, discussed below, and the various embodiments used to describe the principles of the present disclosure in this patent document are by way of illustration only and should not be construed in any way to limit the scope of the disclosure.

Figure 1:
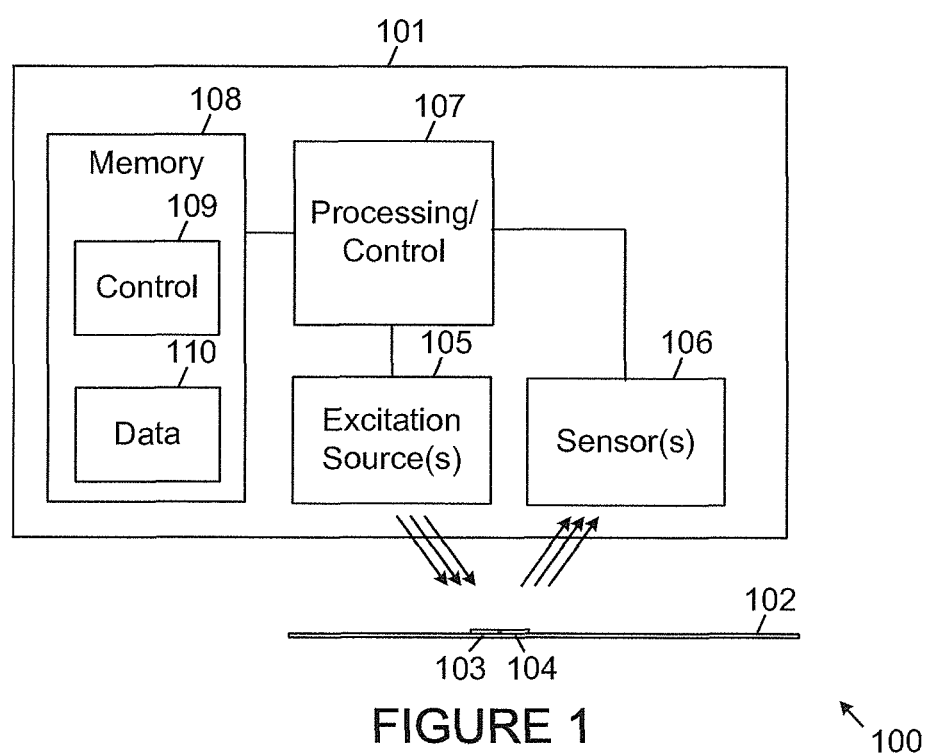
FIG. 1 is a high level block diagram illustrating an authentication system for exploiting security features of multiexponential decays during document authentication according to one or more embodiments of the present disclosure.

FIG. 1 is a high level block diagram illustrating an authentication system for exploiting security features of multiexponential decays during document authentication according to one or more embodiments of the present disclosure. The authentication system 100 includes an authentication device 101, which is preferably configured to be operated by a user as a handheld device (that is, with the components disposed within a body suitable to be handheld and manually operated). The authentication device is employed by the user to authenticate a document 102 on which are affixed, or in which are embedded, a plurality of quasi-resonant luminescent materials 103, 104 within or forming part of a security device for the document 102, as described in further detail below.

Authentication device 101 includes a source 105 of infrared excitation light, which may alternatively be visible or ultraviolet. Preferably the dominant portion of light emitted by source 105 is at or near wavelengths with which luminescent materials 103, 104 are resonant, and which will prompt emission of light by luminescent materials 103, 104. Optical filters may be employed in front of source 105 to increase the selectivity of wavelengths for light impinging on document 102 and the security features including luminescent materials 103, 104. Source 105 may actually be formed of multiple individual but coordinately operated light sources, such as for example a row of light emitting diodes (LEDs).

Authentication device 101 also includes one or more sensors 106 for detecting light emitted by luminescent materials 103, 104. Preferably sensors 106 are most responsive to light at or near wavelengths emitted by luminescent materials 103, 104 in response to excitation light from source 105. Optical filters positioned in front of sensors 106 may improve the selectivity of wavelengths impinging on sensors 106, improving signal-to-noise ratios, and various known signal conditioning and signal processing techniques may likewise be employed to filter the target wavelengths. A plurality of optical sensing devices such as photodiodes may be employed as sensor 106, with the outputs of those sensing devices either summed or averaged for use in authentication.

An integrated circuit processing and control element 107, such as a programmable microprocessor or microcontroller, is coupled to both excitation source 105 and sensors 106, and controls operation of both. That is, processing/control element 107 controls actuation of excitation sources 105 and sampling of the output(s) of sensors 106. The processing/control element 107 is coupled to a memory 108, which may hold both a control program 109 stored in a preferably non-volatile but reprogrammable portion of memory 108 and a data store 110. Although depicted as separate components in FIG. 1, all or some portion of memory 108 may be formed within same packaged integrated circuit as processing/control element 107. Moreover, while depicted as mounted within authentication device 101 in the exemplary embodiment of FIG. 1, processing/control element 107 and/or memory 108 may actually be part of a separate data processing system, with handheld authentication device 101 functioning as a peripheral device to that data processing system can processing/control element 107 coupled by connectors or wireless data communication to excitation source 105 and sensors 106. In addition, to the extent that processing/control element 107 and memory 108 are internal to handheld authentication device 101, a wired or wireless communication port (not shown) may allow handheld authentication device 101 to transmit data to an external data processing system (also not shown in FIG. 1), so that a portion of the processing described below may be performed in that system.

Those skilled in the art will recognize that the complete structure and operation of an authentication system is not depicted in the drawings or described above. Instead, for simplicity and clarity, only so much of an authentication system as is unique to the present disclosure or necessary for an understanding of the present disclosure is depicted and described herein. In addition, while the exemplary embodiment relates to authentication of security features on documents, the principles of the present disclosure may be readily applied to security features in a wide variety of articles, including liquids as well as solid articles.

Luminescent materials 103, 104 in the exemplary embodiment are preferably affixed to document 102 in the form of one or more inks applied to the document 102. Alternatively, however, the security feature may be included in one or more of a fiber, substrate, opacifying layer, label, hologram, or thread forming part of document 102. Although diagrammatically depicted in FIG. 1 as affixed to separate portions of document 102, in practice the two materials may be intermingled across a single region of the surface area of document 102. To the extent excited by different wavelengths or different ranges or wavelengths of light, luminescent materials 103, 104 are preferably excited by (or resonate to) wavelengths at or near each other or to overlapping ranges of wavelengths, with excitation source 105 emitting light predominantly at those wavelengths. Similarly, to the extent that luminescent materials 103, 104 emit light at different wavelengths when excited by a common source or concomitant sources, the wavelength(s) of the emitted light are preferably at or near each other or within overlapping ranges of wavelengths, at amplitudes measurably detectable by sensors 106.

Luminescent materials 103, 104 are photoluminescent (fluorescent and/or phosphorescent), emitting light as a result of absorption of photons within light from the excitation source 105. Luminescent materials 103, 104 exhibit different decay characteristics for light emitted in response to light from the excitation source 105. Thus, rather than an intensity y of emitted light conforming to equation (1) above, the combined light emitted from luminescent materials 103, 104 is a biexponential decay of the form $$y = A_1 e^{-t/\tau_1} + A_2 e^{-t/\tau_2}. \quad (2)$$

Luminescent materials 103, 104 thus offer an additional tier of security and authentication reliability as compared to materials exhibiting simple monoexponential decay.

Figure 2:
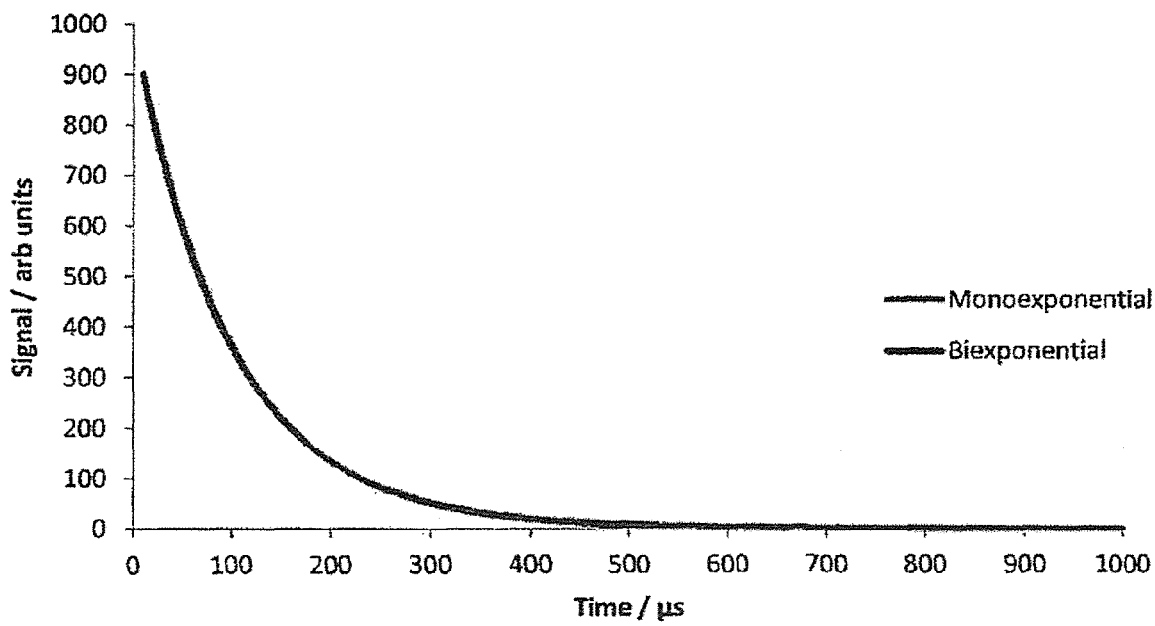
FIG. 2 is a plot comparatively illustrating a typical biexponential decay curve relative to a closely overlapping monoexponential decay curve.

FIG. 2 is a plot comparatively illustrating a typical biexponential decay curve relative to a closely overlapping monoexponential decay curve. The difficulty of differentiating or discriminating between monoexponential and biexponential functions is well known, and is exploited in the present disclosure to provide the additional tier of security and authentication reliability described above. FIG. 2 depicts two curves for a signal measured in arbitrary units as a function of time in microseconds (μs). One of the curves depicted illustrates a monoexponential decay function with a single decay constant $\tau$; the other curve illustrates a biexponential decay function of similar overall decay but with two different decay constants, $\tau_1$ and $\tau_2$. As evident from the plot, the two curves are visually indistinguishable.

Luminescent materials 103, 104 employed for authentication in the present disclosure are characterized different decay constants $\tau_1$ and $\tau_2$ as shown in equation (2) above (e.g., material 103 is characterized by decay constant $\tau_1$ while material 104 is characterized by decay constant $\tau_2$). Depending upon the ratio of the decay constants $\tau_1$ and $\tau_2$ for a biexponential decay function, differences between monoexponential and biexponential decay may not be visually detectable using the unaided human eye, but may be reliably distinguished in a straightforward fashion using sensitive detection equipment and sophisticated signal processing algorithms. If the ratio of the decay constants $\tau_1$ and $\tau_2$ for two different materials is equal to a minimum of about 1.5, the two lifetimes may be separated. Accordingly, the techniques of the present disclosure serve to disguise a sophisticated covert signature as a less sophisticated, still covert signature.

It should be noted that materials with decay constant ratios less than 1.5 are not precluded from functioning in the manner described above within a security feature. Rather, separation of the decay lifetimes in the presence of typical signal-to-noise ratios is simply more consistent and reliable using known signal processing techniques when the ratio is about 1.5 or greater.

Referring once again to FIG. 2, the monoexponential curve illustrated therein represents decay with an initial amplitude A of 1000 (arbitrary units) and a decay constant $\tau$ of about 100 μs. The biexponential curve within FIG. 2 represents the aggregate of a first signal having an initial amplitude $A_1$ of 500 and a decay constant $\tau_1$ of about 80 μs together with a second signal having an initial amplitude $A_2$ of 500 and a decay constant $\tau_2$ of about 120 μs. The ratio of decay constants for the biexponential curve is thus about 1.5. The similarity of the biexponential function in FIG. 2 to the overlaid monoexponential function is evident, and the difference between the two functions is unlikely to be detected by a typical handheld security phosphorescence detection system. Notably, while the magnitude of amplitudes $A_1$ and $A_2$ in the example of FIG. 2 are appreciable, the difference over time for the biexponential function relative to the monoexponential function is vanishingly small.

Figure 3:
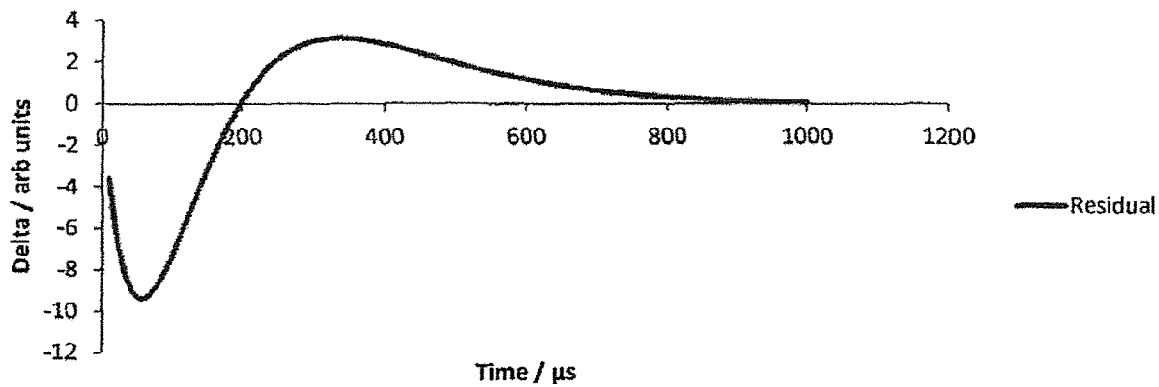
FIG. 3 is a plot illustrating the result of subtracting the monoexponential function plotted in FIG. 2 from the overlaid biexponential function.

FIG. 3 is a plot illustrating the result of subtracting the monoexponential function plotted in FIG. 2 from the overlaid biexponential function. The residual difference ("delta") as a function of time for the difference between the two overlaid functions demonstrates that a difference between the two functions exists, but diminishes as the functions progress toward substantially complete decay. Notably, the magnitude of the delta is very small relative to the dynamic range of the two functions plotted in FIG. 2, spanning about 12 units out of at least 900 units. As a result, sufficient signal-to-noise characteristics must be ensured for differentiation of a biexponential decay from a monoexponential decay.

The biexponential decay security feature described in the present disclosure may be realized in at least two ways. First, a single material with implicit biexponential decay may be manufactured and employed. Alternatively (and preferably), however, mixtures of monoexponential materials may be made at different ratios, yielding a system with inherent biexponential decay security and also offering a number of unique "codes." Thus, for example, if eight different materials each having measurably different decay constants $\tau_1, \tau_2, \tau_3, \tau_4, \tau_5, \tau_6, \tau_7$ and $\tau_8$ are available for pairing in any permutation having an acceptable ratio of decay constants, a large number of distinguishable biexponential decay security features may be implemented. The exact number of possible "codes" depends on the tolerance to which the monoexponential decay constant materials may be manufactured, together with the amplitude resolution of the authentication device 101.

The concepts described above also extend readily to multiexponential decay constants produced by combinations of three, four, or n different materials:

$$y = A_1 e^{-t/\tau_1} + A_2 e^{-t/\tau_2} + A_3 e^{-t/\tau_3} \ldots + A_n e^{-t/\tau_n}. \quad (3)$$

In a mixture of three or more materials, the ratio of the closest pairs of decay constants for materials within the combination should be greater than or equal to about 1.5 to allow reliable differentiation of the materials. That is, where three materials having three different decay constants $\tau_1, \tau_2,$ and $\tau_3$ such that $\tau_1 < \tau_2 < \tau_3$ are employed for a security feature, the ratio of $\tau_2$ to $\tau_1$ should be about 1.5 or greater and the ratio of $\tau_3$ to $\tau_2$ should likewise be about 1.5 or greater. If a fourth material having a decay constant $\tau_4 > \tau_3$ is added, the ratio of $\tau_4$ to $\tau_3$ should be about 1.5 or greater. Thus, although exemplary embodiments described herein relate to use of only two different materials having different decay constants within a security feature, any number of materials may be utilized to form a multiexponential decay constant, subject only to the properties of materials available. As noted above, differentiation when decay constant ratios are less than about 1.5 is possible but more difficult in the presence of typical noise.

Figure 4A:
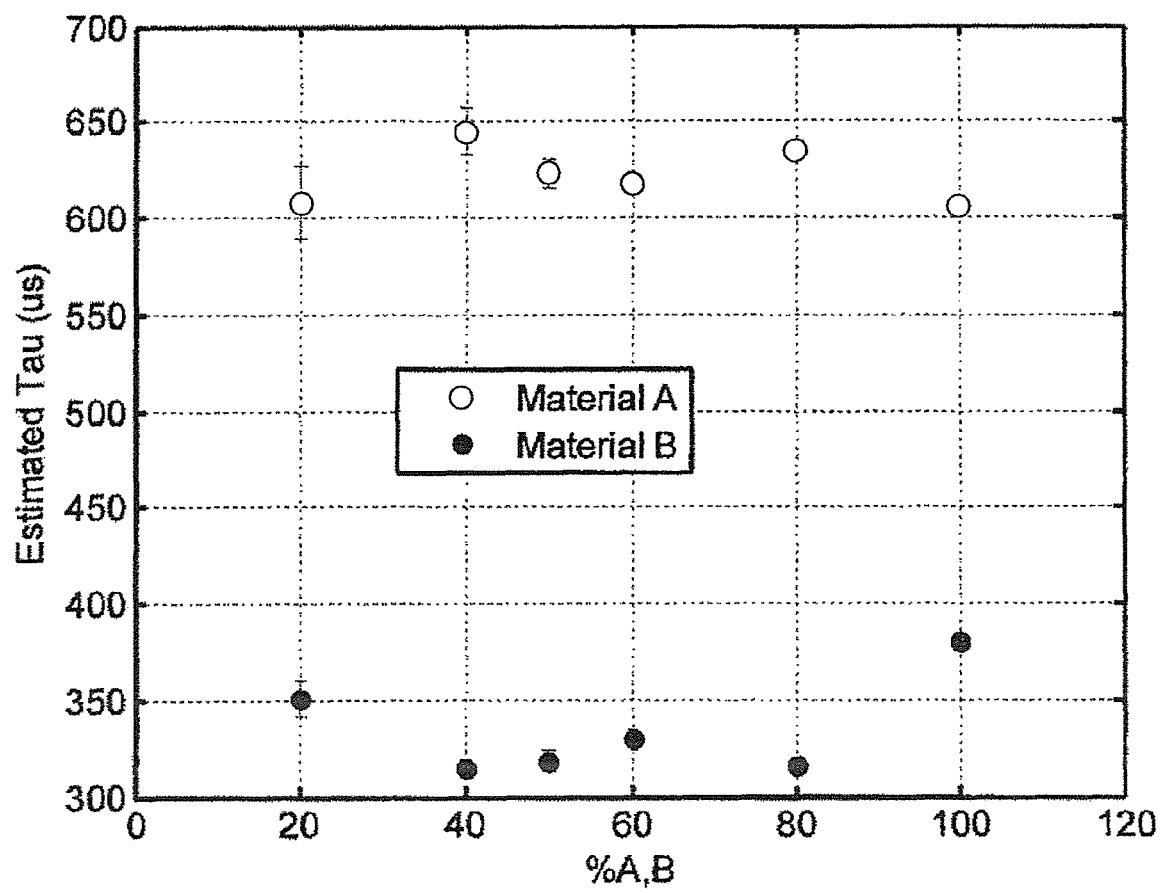
FIGS. 4A and 4B are plots of the decay constants and amplitudes, respectively, for mixtures of two separate monoexponential decay materials in different ratios according to one embodiment of the present disclosure.
Figure 4B:
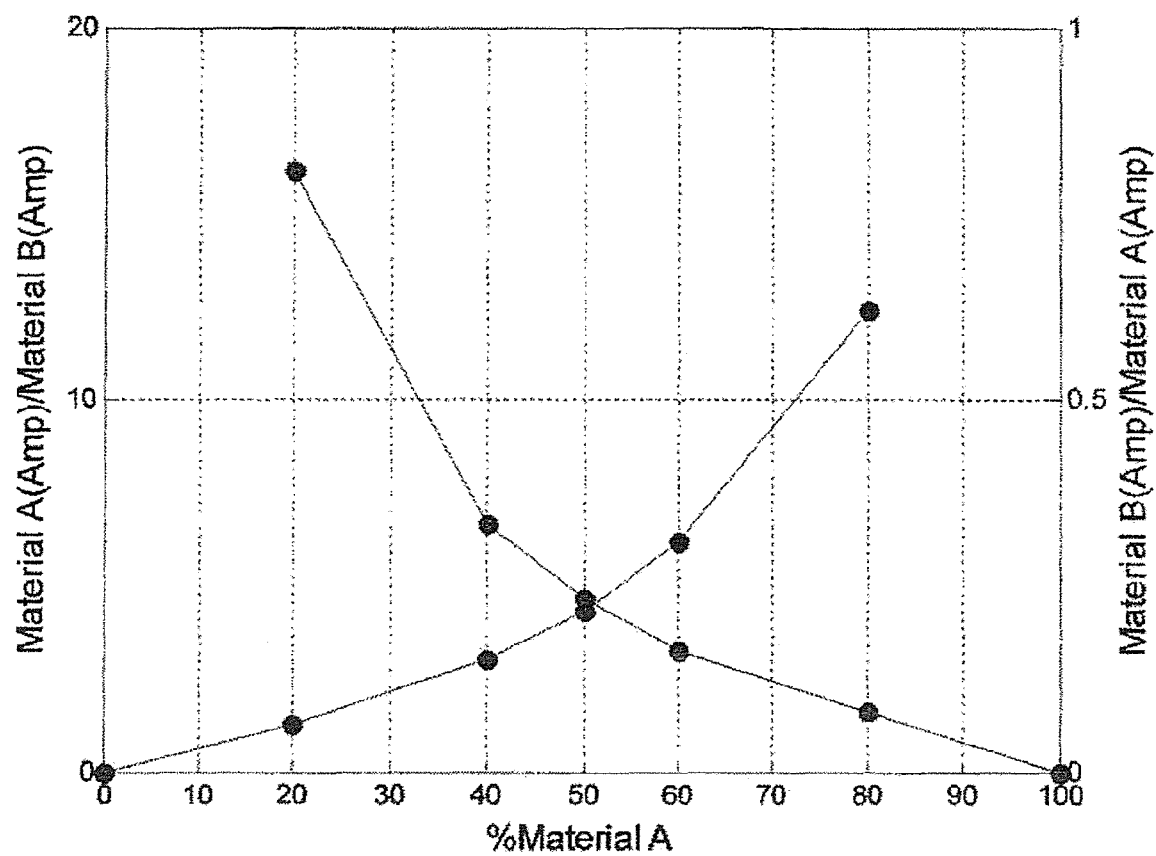

FIGS. 4A and 4B are plots of the decay constants and amplitudes, respectively, for mixtures of two separate monoexponential decay materials in different ratios according to one embodiment of the present disclosure. A number of mixtures of two materials A and B having distinct decay constants $\tau_1$ and $\tau_2$ were formulated into an ink with the following relative concentrations: 0% A and 100% B; 20% A and 80% B; 40% A and 60% B; 50% A and 50% B; 60% A and 40% B; 80% A and 20% B and 100% A and 0% B. Decay spectra were measured with a handheld device and processed to estimate decay constants $\tau_1$ and $\tau_2$, as well as the amplitudes $A_1$ and $A_2$, for each material A and B, respectively. A test statistic detecting the presence of autocorrelation (a relationship between values separated from each other by a given time lag) in the residuals (prediction errors) from a regression analysis, was employed together with curve-fitting to confirm the nature of the exponential decay measurements (i.e., single or double), followed by estimation of the decay constants $\tau_1$ and $\tau_2$.

FIG. 4A shows the estimated decay constants $\tau_1$ and $\tau_2$ for the different ratios of mixtures of materials A and B, while FIG. 4B shows the relative amplitudes. As can be seen from FIG. 4A, the decay constants $\tau_1$ and $\tau_2$ remained consistent regardless of the material concentration. The estimate for decay constant $\tau_1$ for material A was consistently within the range of 600-650 μs, regardless of the relative amount of material A within the overall formulation, while the range of estimates for decay constant $\tau_2$ for material B was generally about 350 μs. Thus, the presence of material A and material B within the security feature may be verified based on the determination of decay constants $\tau_1$ and $\tau_2$ from the measured decay spectra following excitation. Other materials having a distinct decay constant (e.g., in the range of 100-150 μs, or in the range of 450-500 μs) could be substituted for either of material A and material B to formulate a distinct biexponential security feature.

FIG. 4B illustrates the estimates of the amplitudes $A_1$ and $A_2$ for materials A and B based on the measured decay spectra from each ink mixture following excitation, specifically of the ratio of those amplitudes. Plotted on overlaid vertical scales are two curves, one representing the ratio of the amplitude $A_1$ for material A to the amplitude $A_2$ for material B while the other represents the ratio of the amplitude $A_2$ for material B to the amplitude $A_1$ for material A. As evident, the relative concentrations of materials A and B within a given formulation can be determined based on the estimated amplitude ratios. Accordingly, the combination of estimates for decay constants $\tau_1$ and $\tau_2$ and amplitudes $A_1$ and $A_2$ may be employed to distinguish not only the identity of materials A and B within a mixture used for a security feature, but also the ratio of material A to material B within that mixture.

Figure 5:
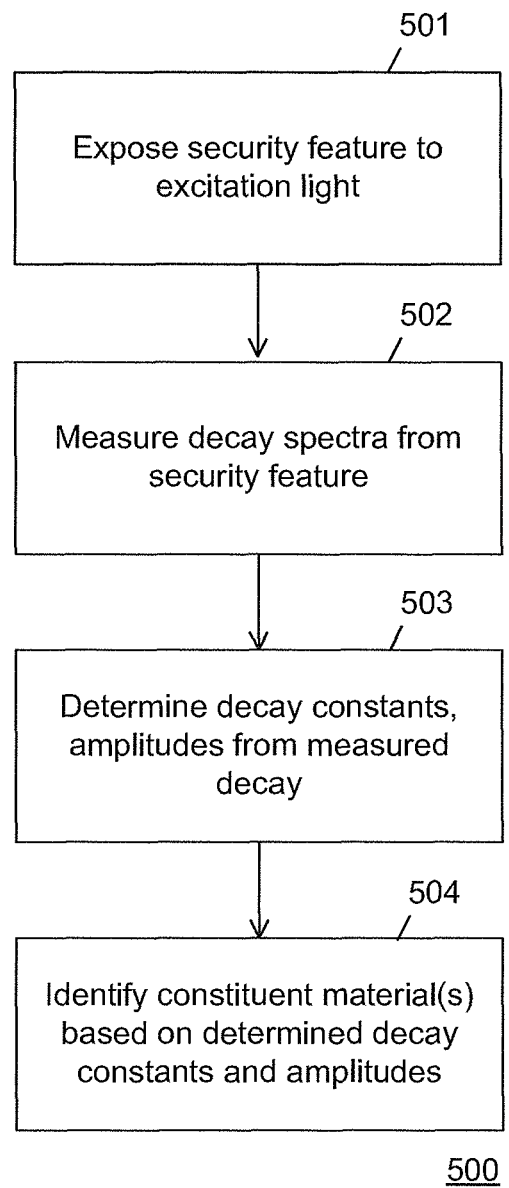
FIG. 5 is a high level flow diagram for detecting multiexponential decays during document authentication according to one or more embodiments of the present disclosure.

FIG. 5 is a high level flow diagram for detecting multiexponential decays during document authentication according to one or more embodiments of the present disclosure. The process 500 begins with exposing the security feature of a document to be authenticated to excitation light (step 501). Such exposure may involve pulsing the excitation source, or continuous actuation of the excitation source for at least a minimum time period. Once exposure to the excitation light is terminated, the decay spectra for the emissions from the security feature being tested are measured (step 502). The measurements involve sampling with at least a predetermined frequency (e.g., every 1 to 100 μs) over a period of 100 to 2,000 μs, depending on the materials employed in the security feature being tested. Estimates of decay constants and amplitudes are then determined from the measured decay data (step 503), in the manner discussed above. Finally, the constituent materials and/or concentrations within the security feature being tested are identified based on the estimated decay constants and amplitudes (step 504). Characteristics of a selected group of materials used for security features may be used to identify the particular materials present in the security feature (or counterfeit thereof), based on the estimated decay constants. The identified combination of materials and concentrations can then be compared to expectations for the security feature, to determine a likelihood of whether the document is authentic.

The present disclosure describes a method of employing multiexponential decay detection in article security and authentication. Specific decay signatures are generated by blending specific decay materials together in particular ratios, to encode a complex biexponential decay signature that nominally appears to be a simplistic monoexponential decay.

The following definitions apply to certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. To the extent definitions for certain words and phrases are provided throughout this patent document, those of ordinary skill in the art should understand that in many, if not most, instances, such definitions apply to prior as well as future uses of such defined words and phrases.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A security feature, comprising:
an intermingled luminescent material comprising a first luminescent material that, when excited in an absence of other luminescent materials, produces emissions with a first exponential decay characteristic and a second luminescent material that, when excited in an absence of other luminescent materials, produces emissions with a second exponential decay characteristic different than the first exponential decay characteristic,
wherein the intermingled luminescent material responds to excitation with emissions at a wavelength having a single multiexponential decay characteristic, the single multiexponential decay characteristic different than the first and second exponential decay characteristics.

2. The security feature according to claim 1, wherein the first exponential decay characteristic is a first decay constant for emissions following excitation and the second exponential decay characteristic is a second decay constant for emissions following excitation.

3. The security feature according to claim 2, wherein the first and second luminescent materials are selected based on a ratio of the first and second decay constants, wherein the ratio of the first and second decay constants is greater than or equal to 1.5.

4. The security feature according to claim 1, wherein the intermingled luminescent material further comprises:
a third luminescent material having a third exponential decay characteristic for emissions following excitation, the third exponential decay characteristic different than the first and second exponential decay characteristics and the single multiexponential decay characteristic.

5. The security feature according to claim 1, wherein the first and second luminescent materials are intermingled in the security feature to produce an overall decay of emissions from the intermingled luminescent material according to $y=A_1 e^{-t/\tau_1}+A_2 e^{-t/\tau_2}$, where $A_1$ is an initial amplitude of emissions from the first luminescent material following excitation, $\tau_1$ is a decay constant for emissions from the first luminescent material following excitation, $A_2$ is an initial amplitude of emissions from the second luminescent material following excitation, and $\tau_2$ is a decay constant for emissions from the second luminescent material following excitation.

6. The security feature according to claim 1, wherein the first and second luminescent materials are present in the security feature in a predetermined ratio of amounts, wherein an overall decay for emissions following excitation from the first luminescent material has a first initial amplitude and decay for emissions following excitation and the second luminescent material has a second initial amplitude, and wherein a ratio of the first initial amplitude to the second initial amplitude is dependent upon the predetermined ratio of amounts.

7. The security feature according to claim 1, comprising one or more of an ink, fiber, substrate, opacifying layer, label, hologram, and thread containing the intermingled luminescent material.

8. A document including the security feature according to claim 1, wherein the document comprises one of a banknote and a security document.

9. A method of authenticating a security feature, the method comprising:
exciting an intermingled luminescent material within the security feature, the intermingled luminescent material comprising a first luminescent material producing emissions following excitation with a first exponential decay characteristic and a second luminescent material producing emissions following excitation with a second exponential decay characteristic different than the first exponential decay characteristic, wherein the intermingled luminescent material responds to excitation with emissions at a wavelength having a single multiexponential decay characteristic, the multiexponential decay characteristic different than the first exponential decay characteristic and the second exponential decay characteristic;
measuring decay spectra from the security feature following excitation;
estimating first and second exponential decay characteristics from the measured decay spectra; and
identifying materials from a selected group of materials corresponding to the first and second estimated first and second exponential decay characteristics forming the single multiexponential decay characteristic.

10. The method according to claim 9, wherein the first exponential decay characteristic is a first decay constant for emissions following excitation and the second exponential decay characteristic is a second decay constant for emissions following excitation.

11. The method according to claim 10, wherein the first and second luminescent materials are selected based on a ratio of the first and second decay constants, wherein the ratio of the first and second decay constants is greater than or equal to 1.5.

12. The method according to claim 10, wherein the first and second luminescent materials are present in the security feature in a predetermined ratio of amounts, the method further comprising:
estimating a first initial amplitude of multiexponential decay for emissions following excitation from the intermingled luminescent material;
estimating a second initial amplitude of multiexponential decay for emissions following excitation from the intermingled luminescent material;
determining a ratio of the first initial amplitude to the second initial amplitude; and
identifying the predetermined ratio of amounts based on the ratio of the first initial amplitude to the second initial amplitude.

13. The method according to claim 9, wherein the intermingled luminescent material further comprises:
a third luminescent material having a third exponential decay characteristic for emissions following excitation, the third exponential decay characteristic different than the first and second exponential decay characteristics and the multiexponential decay characteristic.

14. The method according to claim 9, wherein the first and second luminescent materials are intermingled in the security feature to produce an overall decay of emissions from the intermingled luminescent material according to $y=A_1 e^{-t/\tau_1}+A_2 e^{-t/\tau_2}$, where $A_1$ is an initial amplitude of emissions from the first luminescent material following excitation, $\tau_1$ is a decay constant for emissions from the first luminescent material following excitation, $A_2$ is an initial amplitude of emissions from the second luminescent material following excitation, and $\tau_2$ is a decay constant for emissions from the second luminescent material following excitation.

15. The method according to claim 9, further comprising:
illuminating one or more of an ink, fiber, substrate, opacifying layer, label, hologram, and thread containing the intermingled luminescent material.

16. The method according to claim 15, further comprising:
illuminating a portion of one of a banknote and a security document.

17. An authentication device, comprising:
an excitation source configured to excite at least first and second luminescent materials within a security feature, the first luminescent material, when excited in an absence of other luminescent materials, producing emissions having a first exponential decay constant and the second luminescent material, when excited in an absence of other luminescent materials, producing emissions having a second exponential decay constant, the second exponential decay constant different than the first exponential decay constant, wherein emissions produced at a wavelength following excitation by the first and second materials have a single multiexponential decay constant, the single multiexponential decay constant different than the first and second exponential decay constants;
at least one sensor configure to measure decay spectra from the security feature following excitation; and
a processing element configured to estimate first and second estimated exponential decay constants from multiexponential decay corresponding to the measured decay spectra and to identify materials from a selected group of materials corresponding to the first and second estimated exponential decay constants.

18. The authentication device according to claim 17, wherein the excitation source is configured to illuminate a printed feature on a document, and wherein the first and second luminescent materials are intermingled within ink for the printed feature.

19. The authentication device according to claim 17, wherein the first and second luminescent materials are present in the security feature in a predetermined ratio of amounts, and wherein the processing element is further configured to:
estimate a first initial amplitude of multiexponential decay for emissions following excitation from the first and second luminescent materials,
estimate a second initial amplitude of multiexponential decay for emissions following excitation from the first and second luminescent materials,
determine a ratio of the first initial amplitude to the second initial amplitude, and
identify the predetermined ratio of amounts based on the ratio of the first initial amplitude to the second initial amplitude.

20. The authentication device according to claim 17, disposed within a handheld body.

* * * * *